US008969087B2

(12) United States Patent
Bland et al.

(10) Patent No.: US 8,969,087 B2
(45) Date of Patent: Mar. 3, 2015

(54) METHOD OF PRE-TREATMENT AND STAINING OF A BIOLOGICAL SAMPLE AND DEVICE FOR SUPPORT OF A BIOLOGICAL SAMPLE AND METHODS OF USING SUCH DEVICE

(75) Inventors: Loren L. Bland, Carpinteria, CA (US); Marc E. Key, Ojal, CA (US); Lars Winther, Smoerum (DK); David A. Stanforth, Camarillo, CA (US); Martin N. Lindberg, Måløv (DK)

(73) Assignee: Dako Denmark A/S (DK)

( * ) Notice: Subject to any disclaimer, the term of this patent is extended or adjusted under 35 U.S.C. 154(b) by 3 days.

(21) Appl. No.: 13/605,228

(22) Filed: Sep. 6, 2012

(65) Prior Publication Data
US 2012/0330564 A1    Dec. 27, 2012

Related U.S. Application Data

(63) Continuation of application No. 11/168,987, filed on Jun. 28, 2005, now Pat. No. 8,283,176.

(60) Provisional application No. 60/583,680, filed on Jun. 29, 2004.

(51) Int. Cl.
| | | |
|---|---|---|
| G01N 33/00 | (2006.01) | |
| G01N 1/30 | (2006.01) | |
| B01L 3/00 | (2006.01) | |
| G01N 1/31 | (2006.01) | |
| G01N 35/00 | (2006.01) | |

(52) U.S. Cl.
CPC . *G01N 1/30* (2013.01); *B01L 3/545* (2013.01); *G01N 1/312* (2013.01); *G01N 35/00732* (2013.01); *B01L 2300/023* (2013.01); *B01L 2300/024* (2013.01); *B01L 2300/0822* (2013.01); *G01N 2035/00782* (2013.01)
USPC .............. 436/63; 422/68.1; 422/500; 422/63

(58) Field of Classification Search
CPC ................... B01L 2300/023; B01L 2300/024; B01L 2300/0822; B01L 3/545; G01N 1/30; G01N 1/312; G01N 2035/00782; G01N 35/00732
USPC ................ 422/500, 502, 50, 68.1, 63; 436/63
See application file for complete search history.

(56) References Cited

U.S. PATENT DOCUMENTS

| | | |
|---|---|---|
| 5,355,439 A | 10/1994 | Bernstein et al. |
| 5,675,715 A | 10/1997 | Bernstein et al. |

(Continued)

*Primary Examiner* — Sam P Siefke
(74) *Attorney, Agent, or Firm* — Finnegan, Henderson, Farabow, Garrett & Dunner LLP.

(57) ABSTRACT

There is disclosed a method of pre-treatment and staining, according to a protocol, of a biological sample disposed upon the surface of a carrier, the method comprising the step of recording at least one parameter relating to at least one protocol step in a non-volatile memory located either upon or within the carrier or a device incorporating the carrier. Also disclosed is a device comprising: a non-volatile memory; a surface of the device adapted to carry a biological sample; and communications means electrically coupled to the memory for enabling data transmission to or from an external apparatus. Also disclosed is a method of controlling processing of a biological sample disposed upon a carrier, comprising: providing, upon or within the carrier or an apparatus holding the carrier, a non-volatile memory having information relating to sample processing priority or protocol; reading the information; and scheduling the processing based upon the information.

13 Claims, 4 Drawing Sheets

(56) References Cited

U.S. PATENT DOCUMENTS

| | | |
|---|---|---|
| 5,696,887 A | 12/1997 | Bernstein et al. |
| 5,737,499 A | 4/1998 | Bernstein et al. |
| 6,175,752 B1 * | 1/2001 | Say et al. ............ 600/345 |
| 7,303,725 B2 | 12/2007 | Reinhardt et al. |
| 7,468,161 B2 | 12/2008 | Reinhardt et al. |
| 8,676,509 B2 | 3/2014 | De La Torre-Bueno |
| 2005/0009122 A1 * | 1/2005 | Whelan et al. ............ 435/7.32 |
| 2006/0153736 A1 * | 7/2006 | Kalra et al. ............ 422/57 |

* cited by examiner

METHOD OF PRE-TREATMENT AND STAINING OF A BIOLOGICAL SAMPLE AND DEVICE FOR SUPPORT OF A BIOLOGICAL SAMPLE AND METHODS OF USING SUCH DEVICE

CROSS REFERENCE TO RELATED APPLICATION

This application is a continuation of application Ser. No. 11/168,987, filed Jun. 28, 2005, which claims, under under 35 U.S.C. 119(e), the benefit of the filing date of U.S. Provisional Application No. 60/583,680, filed Jun. 29, 2004 and titled "A Method of PreTreatment and Staining of a Biological Sample and Device for Support of a Biological Sample and Methods of Using such Device," both of which applications are incorporated by reference herein in their entirety.

FIELD OF THE INVENTION

The present invention relates to a method of pre-treatment and staining of a biological sample and a device for support of a biological sample, such as a microscope slide. The invention further relates to various uses for such device.

BACKGROUND OF THE INVENTION

It has already become a well-known feature to provide readable (and/or write-able) labels to microscope slides. Such labels may typically bear a bar code or clear text, indicating information, such as a name of a patient, relating to one or more samples on a microscope slide.

For example, U.S. Pat. No. 5,561,556 (Weissman; Oct. 1, 1996) discloses a slide analysis system with slide having self-contained microscope analysis information. A microscope slide having a pathology specimen thereon includes a machine-readable high density recording medium in the form of a magnetic strip, optical reading strip or the like. The read-write system further embodies elements for operative connection to a microscope system whereby a computer generated representation of the screening history of a pathology specimen is recorded and maintained during pathology analysis of the slide showing the mode and parameters of the analysis as well as position related events of interest. The computer generated screening representation is written to the recording medium by the read-write system, for constant proximate availability with the slide. The recording medium comprises sufficient capacity for encoding with patient identification and medical history information, and slide diagnostic information and analysis for pathological review of the particular pathology specimen on the slide. Compatible read-write systems permit reading and editing of recording media encoding for slide analysis at any time or place without requirements of correlative external files. The slide may comprise a label having some information written or printed in clear text and a magnetic strip or other machine-write-able and readable recording medium either directly below the label or arranged on the opposite side of the slide. This cited document does not consider the pre-treatment and staining process.

In another example, PCT Patent Publication WO 99/10763 A1 discloses a sample holder, which can process data and a method for analysing samples. The samples in question are biological samples such as tissue or body fluids to be examined by use of a microscope, and typically for diagnostic purposes, such as substantiating a cancer diagnosis. The sample holder has two areas; a first area for receiving the sample and a second area for identifying the sample. Said second area is provided with a writeable, readable, non-volatile memory, for example a smart chip, including an electronic circuit and a memory. The electronic circuit may comprise contacts or enable reading and writing of data by other means e.g., by inductive, capacitive or optical means.

In the above cited publication WO 99/10763 A1, it is also suggested to store information relating to the requested/specified sample examination, the manner, technique and execution steps of examination, report data, organisation data, and graphic data that are generated during the examination under a microscope and during a subsequent image processing, e.g., coordinates of reference points for the microscope on the sample surface, coordinate specific relations between examinations and examination results (multidimensional mapping information) e.g., cell maps, nucleic maps, gene maps, or protein maps, images of the samples.

The European Patent Application Publication EP 637 750 A2 (Feb. 8, 1995) discloses a method for analysis of liquid samples whereby data of high information density are arranged on containers with reagent solutions. The data serves to execute and control the analysis. Further disclosed in the above-cited European Patent Application Publication is a method for providing reagent containers with code carriers and a system for analysis of liquid samples using the reagent containers having code carriers. The code may be a bar code or a chip card, e.g., a contact free chip card applying a receiving/transmitting antenna coil.

Further, PCT Patent Application Publication WO 03/040697 relates to and considers the problems of cross-referencing identification of object supports for microtomed analytical samples and the generation of identification.

Also, articles having RF antennas are well known, e.g. from U.S. Pat. No. 6,353,420; inventor, Kevin Kwong-Tai Chung, titled "Wireless article including a plural-turn loop antenna."

SUMMARY OF THE INVENTION

The present invention includes a variety of aspects, which may be combined in different ways. The following descriptions are provided to list elements and describe some of the embodiments of the present invention. These elements are listed with initial embodiments; however it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention provides a method of pre-treatment and staining of a biological sample and a device for support of a biological sample, the device further comprising a memory. Further the present invention provides a method of using the inventive device.

The device may be any kind of support for a biological sample to be prepared for an analysis. Typically the support will be a microscope slide for In-Situ Hybridization (ISH), Immunohistochemistry (IHC), PAP, H/E, and/or special stains. Further, the support may be a tissue array, a micro array, a dot array, a tray, a Petri dish, or at least similar to these items.

The memory may be any kind of memory able to store data, and even possibly a kind belonging to the group comprising electronic, electromagnetic, magnetic, optical or mechanical information storage components. The memory may be of the type "read only", "read and write" and "read, write and rewrite" or combinations thereof. In embodiments, the memory is a "read and write" type able to be updated for every processing step the sample is subjected to.

The memory may be attached to the upper or lower surface of the sample-supporting device. In another embodiment, the memory is embedded in the sample-supporting device.

The memory may be embedded in a label to be attached to the sample-supporting device.

The memory may be permanently or even semi permanently attached to the sample-supporting device. For example, the memory may be embedded in or attached to a rack, clamp, chamber or frame to be attached to one or more slides. In an embodiment, the memory may be detached and prepared for re-use later on a new set of slides.

In other embodiments, the memory is an electronic memory that is readable and write-able. The electronic memory may be part of an electronic device of the kinds used in chip cards. In an embodiment, the electronic device may include a data processing unit, such as a CPU or microprocessor.

The memory and/or electronic device may be accessible through solid electrically conducting contacts arranged in the surface or at an edge of the device. However, in an embodiment, it may be accessed through a wireless connection such as a combination of transmitters and receivers for electromagnetic waves, e.g., using RF antennas, such as coils, or optical, e.g., infrared communication.

The memory may be accessible only through an RF antenna embedded in the device. This configuration is advantageous, as the memory, attached electronic circuitry and RF antenna may be totally embedded in the device. In this manner, the chemically active reagents used for processing the sample in order to prepare the biological sample for the final examination by use of a microscope or electro-optical imaging system cannot get in touch with any parts of the memory, and/or attached electronic circuitry and/or RF antenna.

In an extremely simple version of an embodiment in accordance with the present invention, the storage of information might be in the form of a mechanical printing or punching of symbols or holes, representing events, such as specific steps during a processing and/or identification numbers, representing persons, equipment and/or processing steps. Such systems are known e.g., from punch cards which may be read manually or by mechanical or optical scan systems. The memory could be as simple as a label carrying a plurality of printed or punched symbols and a plurality of blank fields for adding further symbols.

However, a data memory having a high data capacity able to store and add data a plurality of times and even images may be preferred.

According to the invention, this device may be used for reading and writing data relating to the sample. The data can be data relating to the person from whom the sample originates. Further, the data may be data occurring during the sample preparation as well as during any storage time, as well as data occurring during and/or after the analysis of the sample. When using a memory of high capacity, a large plurality of new possibilities, such as storage of images, are provided.

The Owner (e.g., a scientific institution) of a sample or the person from whom the sample originates may provide personal information as well as specific directions for who may access and use the sample, or for which purposes the sample may be used. The memory may contain a plurality of information arranged in hierarchic layers, requiring specific authorisation, in such manner that only a few trusted persons can access certain confidential layers.

During processing in a sample processing instrument, such as an automatic stainer, the instrument could be programmed to read data from the memory every time the new processing step may become initiated or at least when initiating one or more specified steps.

In this manner, an instrument could read in the memory information indicating the processing protocol to be followed and the processing steps already passed and thereby control at which time this device (microscope slide) is ready for this next step. It would be possible to enter data for the time when this next step is initiated, and e.g. a temperature if relevant to the process. When the step is finished, the time could again be written into the memory, e.g. together with a code indicating the newly executed processing step, and possibly a code indicating any reagent container providing a chemical reagent for the process step. If this writing into the memory is done for every step, it could be possible to verify that the instrument is working properly. This could also be applied for trouble shooting if an instrument appears to provide failures. Such a feature could highly improve the safety and quality of the staining and the final analysis result.

It should be understood that a slide with the capacity of the invention might accommodate a reference sample or standard biological sample to be treated. Thereby the slide may be used for validation of specific aspects of the staining process.

A memory attached to a sample-supporting device may be helpful in the management of storage facilities wherein the slides or carriers with biological samples are kept, maybe for a short period of a few minutes, maybe for a long period of several days, weeks or years. Proximity-sensitive sensors may locate the sample-supporting devices in the storage facility. Furthermore, the memory may hold information about the history of the sample, e.g., when and who examined the sample on the device and when it has been inserted and removed from the storage facility and at which location or equipment the examination occurred.

Information regarding the actual reagent containers providing the chemical reagents used for staining of the sample could also be stored in the memory of the device. Such information could reveal any faulty reagent container providing a poor staining.

A memory could also allow for storing digital images of the sample. The digital image storing could be done both at the very beginning of the sample processing when the image could be used for deciding the required amount and location of reagents, and at the end when the image may be used for a (preliminary) analysis and evaluation of the sample as well as a computer programmed "counting" of stained cells providing a computerized "score" for final analysis.

In embodiments, every process step could be registered in the memory of the slide. Thereby the robot or a computer controlling the instrument may check the identity of the slide and check which type of processing the slide is subjected to, how far this slide has come during the processing, or which step the slide has reached, and the computer (or operator) in control of the instrument can then conclude what should be the next process step—according to the specified protocol for the processing—e.g. in a dialog between the memory chip in the slide and the computer controlling the instrument. In a particularly advantageous embodiment, the computer in the instrument may provide for a dialog between slides in a plurality of slides in a section of an instrument. Instead of a scheduling system in the processing instrument itself, the decision regarding which slide to process first may be taken as a result of a communication between the memories of the slides, by requesting their priority and their need for heating, dipping in specific baths, rinsing etc. Such solution may require that the slide contain the full protocol specifying the processing. The processing instrument may then be an automatic instrument providing heat, wash or rinsing, and dispensing reagents on demand from the slide.

DETAILED DESCRIPTION OF THE PREFERRED EMBODIMENTS

Example A

Figure 1:
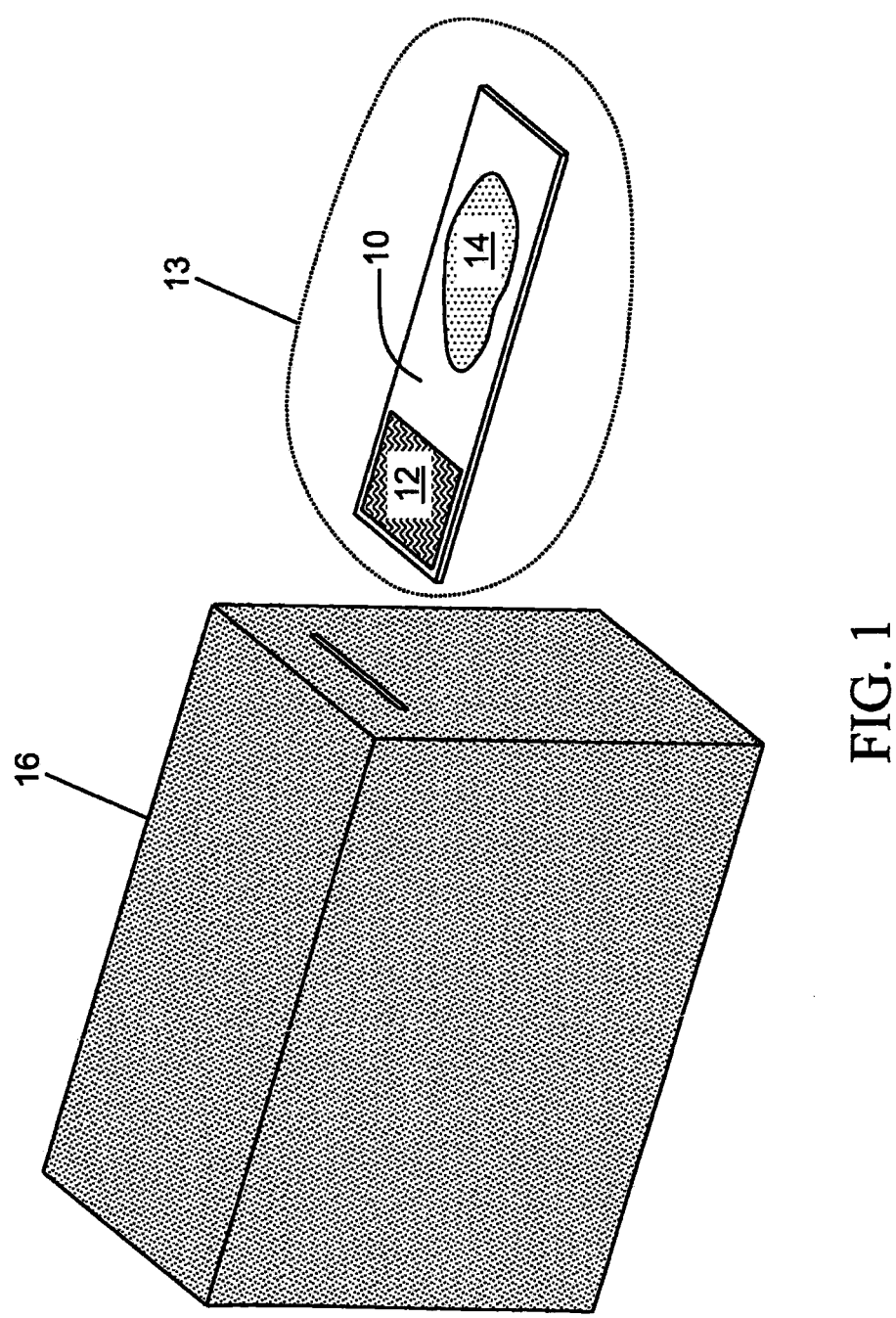
FIG. 1 shows a schematic view of a first embodiment of a slide according to the invention.

FIG. 1 shows a schematic view of a first preferred embodiment 13 of a memory device according to the invention ready to be inserted into a reading and writing device. In a first embodiment according to the present invention, a transparent microscope slide 10 typically but not limited to the typical (approximately 1 inch wide×3 inches long×0.039 inches thick) size used in medical laboratories, has connected to it a computer memory "chip", card or microprocessor 12 (or combination of those devices) capable of storing data and/or images that have been "scanned" or otherwise "read" from or that relate to the contents 14 of the slide.

Information and/or data may either be "written" to the memory or microprocessor or extracted from it by using an external "reader/writer" 16.

Example B

In a second preferred embodiment according to the present invention, a microcircuit with memory may be "embedded" into a slide, that is, a glass (or alternatively plastic) slide could be fabricated around the circuit with no part of the circuit exposed. This could make it impervious to chemicals, corrosion and the like.

Further, an electrical interface between a slide and a reader could be RF (radio frequency). In embodiments, RF antennas might be imbedded along with the microcircuit and memory into the slide.

Example C

Figure 2:
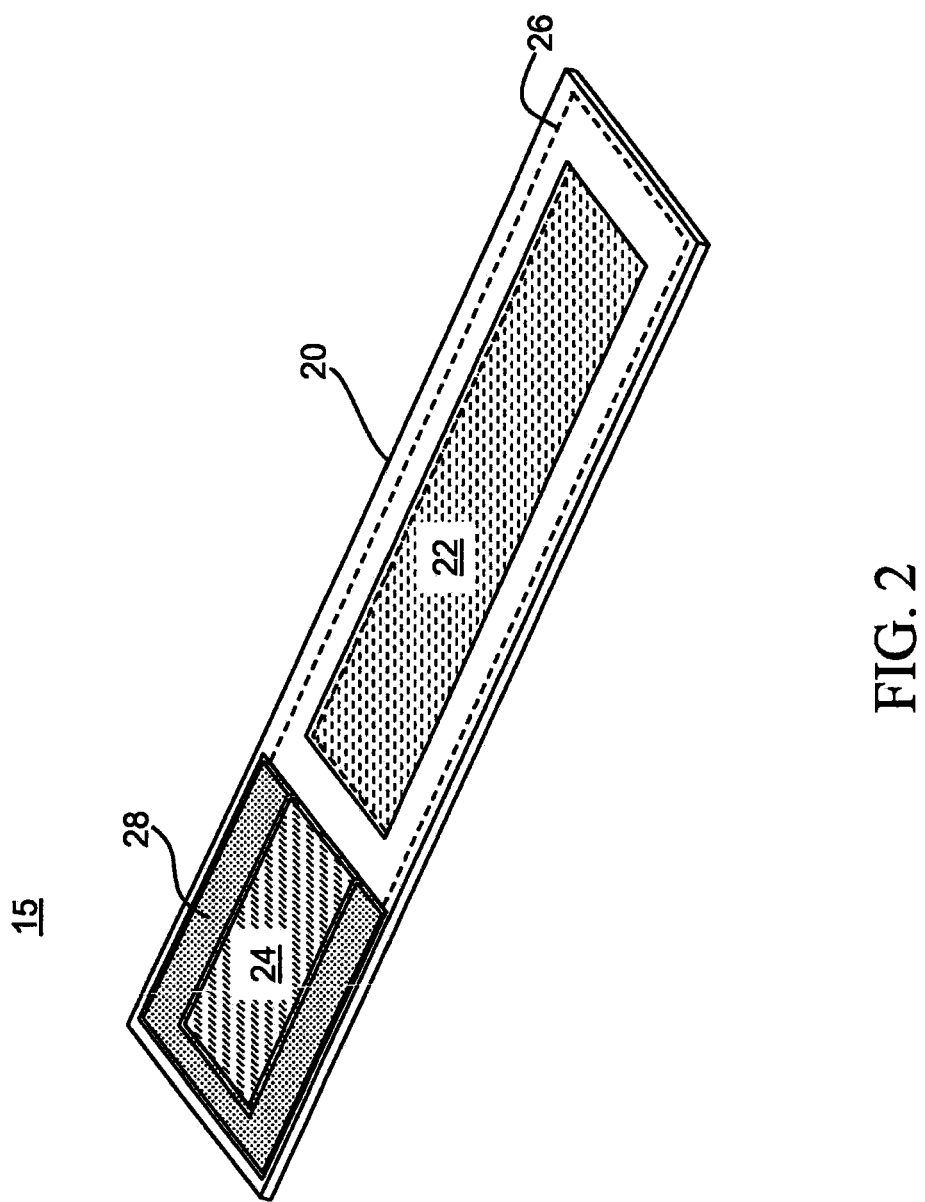
FIG. 2 shows another embodiment of a slide according to the invention.

FIG. 2 shows a third preferred embodiment 15 according to the present invention. The device may comprise a tray 20 having a rectangular field 22 having the size of a standard glass microscope slide, and adapted to carry a biological sample, such as an organic specimen or tissue-section.

Alternatively, a tray may comprise a recessed or grooved area or field 22 of a size adapted to receive a standard glass microscope slide. In a second field 24, a memory may be embedded in the tray 20. The memory may be part of an electronic chip or electronic circuit 28.

An interface between memory and a reader and/or writer may comprise a wireless connection, e.g. comprising an RF circuit 28 and an RF-loop antenna 26 embedded in the tray along the edges of the tray, or an optical connection, such as an infrared port.

A memory device (microscope slides having a memory chip) may be processed on many types of sample processing instruments provided with reading and writing capabilities for accessing the memory in the memory device. Such instrument could be a rectangular box like instrument having drawers or racks with slide holders, such as shown in FIG. 3, or a carousel instrument or other instruments having arrangements for holding and/or storing sample carriers during various chemical treatments.

Figure 3:
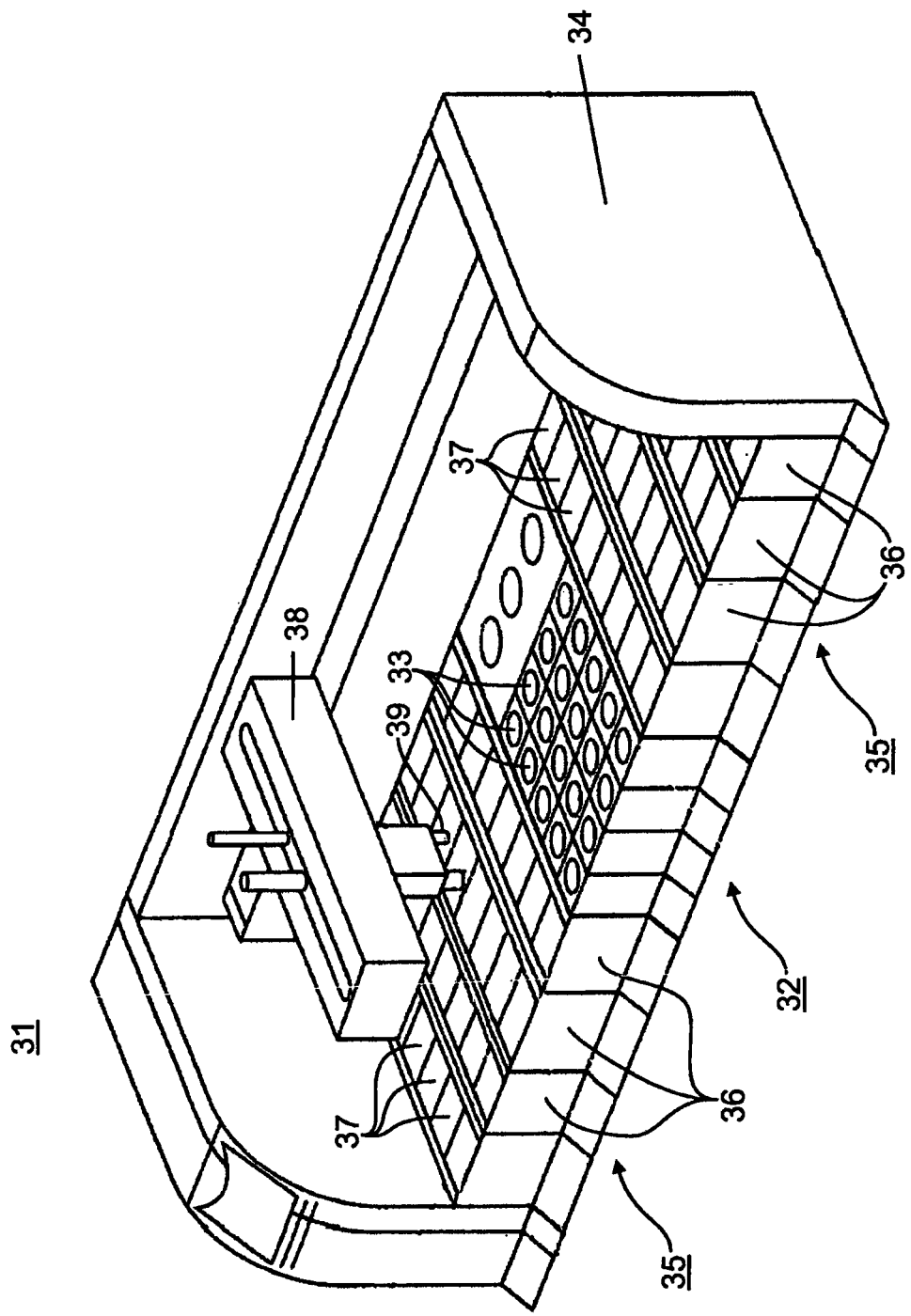
FIG. 3 shows an example showing an automatic stainer having a robotic arm.

An instrument in FIG. 3 is a staining apparatus 31 comprising a rectangular frame 34 surrounding a first station 32 comprising an array of compartments wherein each compartment contains a reagent vial or bottle 33, and two second stations 35 within which a number of separate racks 36 are placed, and where each rack comprises a number of microscope slides 37 mounted side by side in the rack 36. In an embodiment shown, each rack may hold up to eight slides, but the rack may be designed to hold any suitable number of slides. With eight racks arranged side by side, the shown embodiment may hold up to 64 slides 37 each having a sample, e.g. a tissue mounted on the upper side of the slide, so that reagent may be applied from above to the sample on each slide. Of course, other slide arrangements are possible. The instrument may further comprise a robotic arm 38 provided with a reading and writing facility 39 that can be moved so that it is located close to a specific slide when reading or writing in the memory of the slide. The staining apparatus of FIG. 3 is described in greater detail in international patent application publication WO 2004/058950 A1, in international patent application publication WO 2004/059287 A2, in international patent application publication WO 2004/058404 A2, in international patent application publication WO 2004/059284 A2, in international patent application publication WO 2004/057307 A1, and in international patent application publication WO 2004/057308 A1, each of which is incorporated by reference herein in its respective entirety.

A carousel-instrument, e.g. as known from several US patents e.g. U.S. Pat. No. 6,183,693, incorporated by reference herein in its entirety, may also be provided with a reading and writing facility typically arranged at the periphery of the carousel carrying the slides and, by rotation of the carousel, any specific slide may be arranged close to the reading and writing facility. In an alternative embodiment, a reading and writing facility may include a rotate-able directional antenna or a controllable phased array antenna able to direct a signal to a location of a specific slide in an instrument, e.g. an instrument without robotic arm or movable carousel.

The inventive device may be used as a carrier, such as a microscope slide, in apparatus for the processing of biological samples on carriers, and the memory of the device may be applied for storage of information such as, but not limited to:
1. Data of the patient.
2. Priority of the slide—(high priority for an urgent case—e.g. patient still under surgery—versus low priority for simply routine cases and no urgency)
3. Information regarding who (persons—institutions—universities—hospitals and the like) may get access to this sample.

4. Data from the history of the slide, the kind of antibody used, and other details of the pre-treatment and staining.
5. The kind of tissue in the sample.
6. The position of the tissue sample on the slide.

Regarding the history of the slide, the following data may appear to be relevant for storage:

1. During any temporary storage or transport in storage container, a temperature sensor and other sensors might transmit data indicating e.g. temperature, humidity, light, movements, and/or pressure of the environment in the storage container to the receiver in the device. From a receiver the data may be transferred to and stored in the memory in the slide.
2. Information identifying and relating to the instruments used for the staining and the microscope used for analysis, and/or the external database keeping information related to this slide
3. The protocol
4. Any poison or hazardous materials in the tissue—in order to warn about any environmental risks and perhaps even if/when the sample (tissue, cells or similar biological material) is disposed to waste bin.
5. Any other information that could be relevant to future persons using or handling the sample.

Later, after the staining has been completed and a pathologist has analysed the slide, it would be advantageous to enter information from the report prepared by the pathologist, e.g., but not limited to:

1. The diagnosis.
2. The location of specifically interesting portions of the tissue causing the diagnosis.

Below is listed as non-limiting examples a plurality of various information which may be stored on the device:

Identification of the person from whom the sample was taken;
Date, and conditions during the sampling;
Authorisations for specific institutions or persons allowed to do research on the sample;
Specifications relating to a request for examination;
Prioritisation (a specific slide may be given a high priority ensuring fastest possible treatment e.g., if the sample comes from a patient still under surgery);
Specification of one or more (and perhaps even all) steps in the pre-treatment and staining processes carried out for preparing the sample for analysis in a microscope;
Recording of Environmental conditions (temperature, pressure, humidity) during at least one, (and perhaps even all) steps in the pre-treatment and staining processes;
Recording of Environmental conditions (temperature, pressure, humidity) during storage and transport;
Logging all or a plurality of data relating to the pre-treatment and staining of the sample as specified by the protocol defining the treatment of a sample; and
Recording of data relating to the analysis by use of the microscope.

In an embodiment, a method of the action of execution of at least one step of a series of steps in the processing (including pre-treatment and staining) of a biological sample on a carrier may be registered, recorded, and stored in the memory on the carrier.

In other embodiments, a plurality (and perhaps even all) of the execution actions are registered, recorded, and stored in the memory. Further, environmental conditions during at least one processing step, such as temperature, pressure and humidity, may advantageously be stored together with the registration of the execution of a step. In this manner, any faulty condition occurring during a processing may be revealed.

This may be accomplished, for instance, by having sensors connected to data processing equipment, which has been adapted to send relevant data to a data reading and writing device, which may be mounted on a robotic arm, such as robotic arm 38 (FIG. 3), able to reach and co-operate with the input means to the memory on the slide device, e.g. conductive contacts or RF antennas. Alternatively, the electronic chip circuit embedded in the device may include one or more sensors, such as a temperature sensor directly providing temperature data to the memory—e.g. by regular intervals, or by providing time and temperature data when certain limits are reached.

The type of data to be stored may belong to a group consisting of but certainly not limited to: time of occurrence data, number of occurrence data, part of operation data, amount of usage data, amount of material used data, type of material used data, substance identifier data, individual movement data, robotic action data, individual robotic movement data, individual operation data, individual usage data, actual date data, actual time data, precise time data, relative time data, absolute time data, initiation time data, completion time data, subject sample data, sample image data, individual sample process data, individual slide log data, system image data, substance image data, type of protocol data and the like.

A method according to the present invention may comprise systematically storing, in a slide memory, important details of a significant number of said plurality of sample process operations in real time as such sample process operations occur, and perhaps even systematically storing precise time data and/or systematically storing relative time data, systematically storing temperature data, systematically storing image data, and even systematically storing sample image data.

Generally, all data in a memory on a sample carrier according to the invention should be copied to a database connected to the computer in control of the sample processing instrument and/or the microscope used for analysis. Thereby, the data will be ready for any further data processing and the data can be saved in safe manner. A microscope slide may break and in certain cases the memory could be inaccessible or lose the contents.

Also, in view of the fact the size of memory is limited, it could be relevant after a successful completion of the staining process to transfer to a remote database—or possibly delete—all data relating to the staining, so that the pathologist analysing the slide may have an almost empty memory with plenty of space for adding his report.

As an alternative, it may be advantageous to let the data relating to the staining process become replaced by a shortened version, saving important information in a short summary. Such summary could be created by an assisting operator or automatically from a controlling computer, or even by a program in a CPU (data processing unit/computer) in the device.

USE/INDUSTRIAL Applicability

In a new method of processing biological samples, the new memory slide can be very useful. By use of the readable and writeable memory it is possible to register a number (or perhaps even all) process steps in a reading/writing action included in the actions related to a specific execution of a specific processing step in a processing instrument.

In embodiments, every process step could be registered in the memory of the slide. Thereby the robot or a computer controlling the instrument may check the identity of the slide and check which type of processing the slide is subjected to, how far this slide has come during the processing, or which step the slide has reached, and the computer (or operator) in control of the instrument can then conclude what should be the next process step—according to the specified protocol for the processing—e.g. in a dialog between the memory chip in the slide and the computer controlling the instrument.

The memory will enable a better security for providing the correct treatment to the correct slide, thereby increasing the percentage of true positive results and true negative results—and lowering the number of faulty negative and faulty positive results obtained by the pathologists.

Furthermore, the memory slide can enable a particularly advantageous new type of automatic sample processing apparatus, which can operate as a fully continuous apparatus, enabling an insertion of a high-priority slide (e.g. coming from a patient still under surgery). Such high-priority slide can then become included in a new scheduling allowing the high-priority slide to pass through all processing steps as fast as possible while the routine slides will have to spend a few more minutes in a washing bath or similar type of wet condition—which will not deteriorate their treatment, but simply allow them to wait until the high-priority slide has received the newly scheduled fast treatment.

Figure 4:
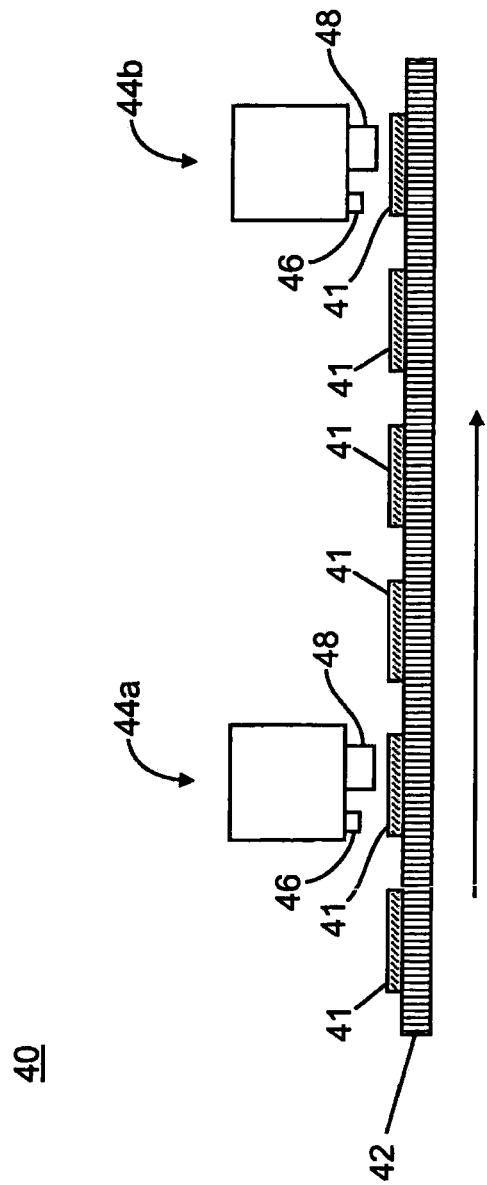
FIG. 4 shows an example of an automated biological sample processing apparatus in accordance with an embodiment of the invention.

FIG. 4 shows an example of an automated biological sample processing apparatus in accordance with an embodiment of the invention. The automated apparatus 40 shown in FIG. 4 incorporates a plurality of sample carrier devices 41 according to the present invention, the sample carrier devices 41 being disposed upon a transport mechanism or moveable slide platform such as, for instance, conveyor belt 42. Each one of the sample carrier devices 41 incorporates a memory element as previously disclosed in this document and could comprise, for instance, either the slide 13 shown in FIG. 1 or the slide 15 shown in FIG. 2.

The transport mechanism 42 within the automated biological sample processing apparatus 40 (FIG. 4) physically positions, in assembly-line fashion, each sample carrier device 41 adjacent to one or more sample processing stations. For instance, as shown in FIG. 4, the slides 41 are delivered, in sequence, to a first sample processing station 44a and to a second sample processing station 44b, as shown by the arrow in FIG. 4. Each such sample processing station comprises a respective sample treatment apparatus 48 for administering at least one treatment to the biological samples and a respective transmitter/receiver device 46 for communicating with the sample carrier devices 41. Although two sample processing stations 44a-44b are shown in FIG. 4, the automated apparatus 40 could, in principle, incorporate any number of such sample processing stations, depending upon the number of processing steps that are required and the requirements of the user.

The treatments administered by the sample treatment apparatuses 48 could comprise, for instance, administration of chemical reagent, administration of heat, administration of a cleaning solution, a buffer solution, rinse water or a jet of air or other gas, cooling of the sample, among others. More broadly understood, a sample "treatment" could comprise a re-routing of a sample carrier device 41 to a second transport mechanism 42 so as to be directed to a particular sample processing station having the required capabilities for performing a particular protocol step.

In the system 40 shown in FIG. 4, the memory element of each sample carrier device 41 retains a record of the protocol to be performed upon the sample as well as records of all the protocol steps that have been carried out upon the sample up to any particular time. When each slide 41 arrives at a sample processing station, the transmitter/receiver device 46 at the sample processing station reads the next protocol step to be performed upon the sample on the slide 41 and directs the sample treatment apparatus 48 to administer such treatment, if applicable. Afterwards, the transmitter/receiver device 46 writes information regarding the just-performed treatment to the memory of the slide 41 and the conveyor 42 transports the slide 41 in the direction of the next processing station and also brings a subsequent slide into proximity to the same sample processing station. Thus, there is little or no need for scheduling software or logic within the automated apparatus 40, since most or all of the required information that controls the sequence of events is carried within the slides 41 themselves.

FIG. 4 indicates that the slides 41 are physically moved in the automated biological sample processing apparatus 40. This configuration may be desirable or useful for a sample processing device utilizing a carousel for sample transport, such as is known for in the art for biological staining. However, since not all protocol steps will necessarily be performed upon all samples for equal time lengths, it may be more advantageous to eliminate the slide transport mechanism 42 and to maintain the plurality of slides 41 on one or more stationary platforms at the same time that a sample processing station 44a is caused to move, relative to the slides, within the apparatus 40. For instance, the sample processing station 44a, the transmitter/receiver device 46 and the sample treatment apparatuses 48 shown in FIG. 4 could all be disposed upon the robotic arm 38 of the staining apparatus 31 shown in FIG. 3. In this alternative situation, the transmitter/receiver device 46 may be the reading and writing facility 39 as shown in FIG. 3. The robotic arm will then position the sample processing station 44a adjacent to each slide 41, according to a pre-determined pattern. While in proximity to a slide 41, the sample processing station reads, from the slide memory, the required next protocol step (if any) to be performed upon the sample carried on the slide and then, if required, initiates or administers the appropriate treatment to the sample on the slide. The robotic arm then positions the sample processing station adjacent to the next slide in the pre-determined pattern. When the sample processing station reaches the last slide, this sequence of events is repeated from the beginning.

In a particularly advantageous embodiment, the computer in the instrument may provide for a dialog between slides in a plurality of slides in a section of an instrument. Instead of a scheduling system in the processing instrument itself, the decision regarding which slide to process first may be taken as a result of a communication between the memories of the slides, by requesting their priority and their need for heating, dipping in specific baths, rinsing etc. Such solution may require that the slide contain the full protocol specifying the processing. The processing instrument may then be an automatic instrument providing heat, wash or rinsing, and dispensing reagents on demand from the slide.

As can be easily understood from the foregoing, the basic concepts of the present invention may be embodied in a variety of ways. It involves both staining techniques as well as devices to accomplish the appropriate stain device. In this application, the staining techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "treatment" should be understood to encompass disclosure of the act of "treating"—whether explicitly discussed or not—and, conversely, were there effectively disclosure of the act of "treating", such a disclosure should be understood to encompass disclosure of a "treatment" and even a "means for treating" Such changes and alternative terms are to be understood to be explicitly included in the description.

As to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference.

The invention claimed is:

1. An apparatus for processing a biological sample comprising:

at least one station configured to receive at least one sample carrier; and
at least one instrument comprising:
    a stainer that dispenses a reagent with a robotic arm;
    a radio frequency transmitter configured to transmit a radio frequency signal to a radio frequency device associated with a sample carrier, the sample carrier having at least one biological sample arranged thereon;
    a radio frequency receiver configured to receive data stored on the radio frequency device via a return signal from the radio frequency device; and
    a computer communication interface comprising a non-transitory memory programmed with instructions that cause the computer communication interface to
        convey the data to a central database in a computer; and
        receive control instructions from the computer to carry out at least one processing step on the biological sample,
    wherein the computer is configured to determine the at least one processing step to be carried out on the biological sample based on the data.

2. The apparatus of claim 1, wherein the data stored on the radio frequency device includes at least one of patient data, carrier priority data, access data, historical processing data for the sample, sample type data, or the position of the sample on the carrier.

3. The apparatus of claim 1, wherein the radio frequency device includes writable memory.

4. The apparatus of claim 3, wherein the laboratory instrument further comprises a writing facility configured to write data received from the computer to the writable memory of the radio frequency device.

5. The apparatus of claim 1, wherein the data further includes information about at least one processing step performed on the sample.

6. The apparatus of claim 1, wherein the computer is further configured communicate with the radio frequency device in order to determine a next processing step.

7. The apparatus of claim 6, wherein the sample carrier includes writable memory, and the laboratory instrument comprises a writing facility configured to write information regarding the processing to the writable memory.

8. The apparatus of claim 1, wherein the radio frequency device is embedded in the sample carrier.

9. The apparatus of claim 1, wherein at least one of the computer and the laboratory instrument comprises a database communication interface configured to transfer to a remote database data relating to the processing performed by the at least one instrument.

10. The apparatus of claim 1, wherein the radio frequency device includes an RF antenna.

11. The apparatus of claim 1, wherein the radio frequency device includes a data processing unit with a microprocessor.

12. An apparatus for processing a biological tissue specimen comprising:

at least one station configured to receive at least one sample carrier; and
at least one instrument comprising:
    a stainer that dispenses a reagent with a robotic arm;
    a radio frequency transmitter configured to transmit a radio frequency signal to a radio frequency device associated with a sample carrier, the sample carrier having at least one biological tissue specimen arranged thereon;

a radio frequency receive configured to receive data stored on the radio frequency device via a return signal from the radio frequency device; and a computer communication interface comprising a non-transitory memory programmed with instructions that cause the computer communication interface to convey the data to a central database in a computer; and receive control instructions from the computer to carry out at least one processing step on the biological tissue specimen, wherein the computer is configured to determine the at least one processing step to be carried out on the biological tissue specimen based on the data.

13. An apparatus for processing a biological sample comprising:

at least one stainer that dispenses a reagent with a robotic arm, comprising:

at least one station configured to receive at least one sample carrier;

a radio frequency transmitter configured to transmit a radio frequency signal to a radio frequency device associated with a sample carrier, the sample carrier having at least one sample arranged thereon;

a radio frequency receiver configured to receive data stored on the radio frequency device via a return signal from the radio frequency device; and a computer communication interface comprising a non-transitory memory programmed with instructions that cause the computer communication interface to convey the data to a central database in a computer; and receive control instructions from the computer to carry out at least one processing step on the sample, wherein the computer is configured to determine the at least one processing step to be carried out on the sample based on the data.

\* \* \* \* \*

UNITED STATES PATENT AND TRADEMARK OFFICE
CERTIFICATE OF CORRECTION

PATENT NO.        : 8,969,087 B2
APPLICATION NO.   : 13/605228
DATED             : March 3, 2015
INVENTOR(S)       : Loren L. Bland et al.

It is certified that error appears in the above-identified patent and that said Letters Patent is hereby corrected as shown below:

In the Claims

Claim 6, Col. 12, Line 40, "configured communicate" should read as --configured to communicate--.

Signed and Sealed this
Eighth Day of September, 2015

Michelle K. Lee
*Director of the United States Patent and Trademark Office*